US006447907B1

(12) United States Patent
Wolter et al.

(10) Patent No.: US 6,447,907 B1
(45) Date of Patent: Sep. 10, 2002

(54) SPHERICAL IONOMER PARTICLES AND PRODUCTION THEREOF

(75) Inventors: Herbert Wolter, Tauberbischofsheim; Carsten Gellermann, Wuerzburg, both of (DE)

(73) Assignee: Fraunhofer-Gesellschaft zur Forderung der Angewandten Forschung e.v., Munich (DE)

( * ) Notice: Subject to any disclaimer, the term of this patent is extended or adjusted under 35 U.S.C. 154(b) by 0 days.

(21) Appl. No.: 09/508,118

(22) PCT Filed: Jul. 22, 1999

(86) PCT No.: PCT/EP99/05257

§ 371 (c)(1),
(2), (4) Date: Jun. 14, 2000

(87) PCT Pub. No.: WO00/05182

PCT Pub. Date: Feb. 3, 2000

(30) Foreign Application Priority Data

Jul. 22, 1998 (DE) .......................... 198 32 965

(51) Int. Cl.$^7$ .............................. B36B 5/16; C08K 3/06
(52) U.S. Cl. .................. 428/402; 428/403; 428/402.2; 428/402.21; 428/404; 428/405; 523/214; 523/216; 523/217
(58) Field of Search ................................. 428/402, 403, 428/402.2, 402.21, 404, 405; 523/214, 216, 217

(56) References Cited

U.S. PATENT DOCUMENTS

| | | | |
|---|---|---|---|
| 4,215,033 A | | 7/1980 | Bowen ...................... 523/115 |
| 4,738,722 A | | 4/1988 | Ibsen et al. .................... 106/35 |
| 5,320,905 A | * | 6/1994 | Vaughn ...................... 428/401 |
| 5,480,573 A | * | 1/1996 | Durfee ...................... 252/78.3 |

FOREIGN PATENT DOCUMENTS

| | | |
|---|---|---|
| DE | 32 47 800 | 4/1983 |
| DE | 38 34 744 | 4/1990 |
| EP | 0 216 278 | 4/1987 |
| EP | 0 363 927 | 4/1990 |

OTHER PUBLICATIONS

Patent Abstracts of Japan, 08091819A, Apr. 9, 1996.
Wilson, A.D. et al., "Aluminosilicate Glasses for Polyelectrolyte Cements", *Ind. Eng. Chem. Prod. Res. Dev.*, 1980, pp. 263–270.
Wilson, A.D. et al., "Glass–Ionomer Cements", Quintessense Publishing Co., Inc., Chapter 2, pp. 21–40, 1988.
Proc. of the 2$^{nd}$ Int. Symp. On Glass–Ionomers, "Glass–Ionomers, The Next Generation", 1994, pp. 13.

(List continued on next page.)

*Primary Examiner*—Leszek Kiliman
(74) *Attorney, Agent, or Firm*—Foley & Lardner

(57) ABSTRACT

The invention relates to spherical or approximately spherical ionomer particles, comprising an inner area and an outer area which contains silicon ions. The cations of said outer area comprise a) at least one element which can occupy lattice sites of the silicon in silicate compounds, producing a negative excess of charge and b) at least one element which is selected from the elements of the first and second main groups and those that can appear in a divalent form and which can compensate for the negative excess of charge. Suitable methods for producing the inventive particles are all those methods for producing spherical or approximately spherical particles from a suspension dispersion, emulsion or similar and separating them from the surrounding solvent. Aerosol methods and especially, spray drying of suitable solutions, gels, sols or dispersions/suspensions can also be used. The inventive ionomer particles are especially suitable for use with acid-containing matrices as cements which can be used advantageously in dentistry for example.

22 Claims, 1 Drawing Sheet

OTHER PUBLICATIONS

Figure 2:
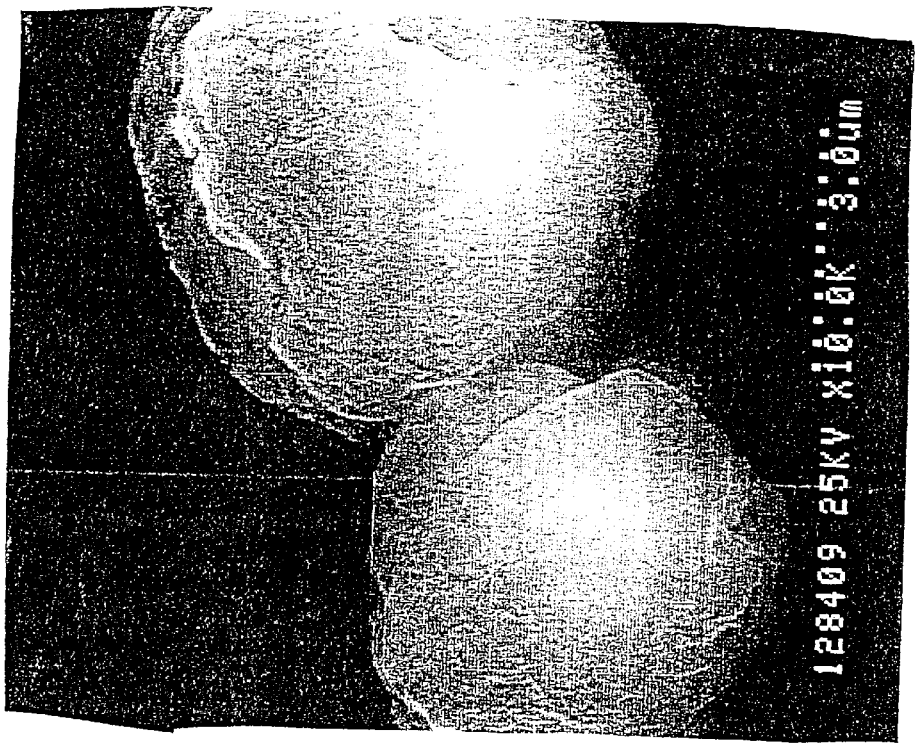

Stöber, A.F. et al., "Controlled Growth of Monodisperse Silica Spheres in the Micron Size Range", *Journal of Colloid and Interface Science*, 26, 1968, pp. 62–69.

Minehan, W.T. et al., "Synthesis of spherical silica particles by spontaneous emulsification", 63, 1992, pp. 181–187.

Osseo–Asare, K. et al., "Preparation of $SiO_2$ Nanoparticles in a Non–Ionic Reverse Micellar System", *Colloids and Surfaces*, 50, 1990, pp. 321–339.

Jayanthi, G.V. et al., Modeling of Solid Particle formation During Solution Aerosol Themolysis;, *Aerosol Science and Technology*, 19, 1993, pp. 478–490.

Berglund, R.N. et al., "Generation of Monodispese Aerosol Standards", *Environmental Science and Technology*, v7, n 2, Feb. 1973, pp. 147–153.

Akinmade, A.O. et al., "Development of glasses for novel polyphosphonate dental cements", *British Ceramic Transactions*, 93(3), 1994, pp. 85–90.

* cited by examiner

SPHERICAL IONOMER PARTICLES AND PRODUCTION THEREOF

The present invention relates to inorganic or possibly organically modified particles which can be subjected to targeted leaching out of certain cations and can thus be used as inorganic components in glass ionomer cements. The invention further relates to novel ways of producing such particles, known as ionomers, and to the cements which can be produced therewith.

For the purposes of the present invention, the term "ionomer particle" refers to inorganic particles which in combination with a preferably acid-containing matrix can be used in a very versatile way as cements (self-curing, light-curable, etc.). For a cement formation reaction to be able to take place at all, these particles have to have a defined or targeted instability, i.e. when combined with water in the presence of a partner with which they are to combine they have to release metal ions which lead to a curing reaction in the partner substance. The composition ranges in which this targeted instability occurs are known to those skilled in the art or can easily be determined, see, for example, the phase diagrams of many systems in "Alumosilicate Glasses for Polyelectrolyte Cements", A. D. Wilson et al., Ind. Eng. Chem. Prod. Res. Dev. 1980, (19) 263–270, or "Glass-Ionomer Cements", A. D. Wilson et al., 1988, Quintessence Publishing Co., Inc., Chapter 2 (p. 21 ff.).

The basic makeup of the usually vitreous ionomers usually comprises the ternary system silicon dioxide-aluminum oxide-calcium oxide. Melting these components together gives particles which undergo a two-stage reaction in the presence of, for example, polyalkenoic acids. Here, calcium ions are firstly leached from the glass composite by the attack of protons of the polyalkenoic acids and are complexed by the carboxylate groups of the polyalkenoic acids in an unstable phase or primary curing. Secondary curing then leads to a stable phase in which aluminum cations now also migrate from the glass ionomer. Hydration of the polysalts occurs and aluminum polyalkenoates are formed. At the same time, the outer shell of the aluminum silicate glasses is dissolved by proton attack to form ortho-silicic acid. During the further course of the reaction, this orthosilicic acid condenses to form silica gel; a gel layer results.

Some of the reactions described are very slow; however, the reaction can be accelerated by addition of fluoride, for example in the form of fluorspar. Hydroxycarboxylic acids, e.g. tartaric acid, can be added as regulators; they lengthen the processing time and shorten the curing time. Further additives such as aluminum phosphate, cryolite or aluminum trifluoride are known as optimizing processing aids.

The known ionomer particles are obtained by melting together the respective starting compounds (mainly oxides). Their microstructure is complex. The milling process to which the fused glass ionomer is subjected in order to obtain the desired particles promotes the formation of sharp-edged, nonspherical particles. This makes the resulting abrasion resistance of the ionomer unsatisfactory. The particles formed have a broad particle size distribution and are relatively large; they usually have a diameter far above three microns. They have to be subjected to a complicated classification process in order to be obtained in a size distribution which is still only acceptable to a degree. Apart from the high expenditure of effort, this means a high loss of material and thus extremely poor yields (even when using a plurality of screening steps or air classification steps, a distribution over less than at least one power of ten is not achieved, if only because of the unfavorable geometry). As a result of the fusion procedure, the aluminum silicate matrix is frequently not homogeneous. Thus, for example, fluorides are embedded in the form of droplets rich in calcium fluoride.

Classical glass ionomer cements having purely inorganic curing, light-curable glass ionomer cements (with additional organic polymerizable components) and compomers (the term is derived from the contraction of the expressions composite and ionomer and is used to refer to cements in which the carboxyl group used is bound to the same molecule which also bears a crosslinkable double bond, see, for example, "Glasionomers, The next Generation", Proc. of the 2nd Int. Symp. on Glass Ionomers, 1994, p. 13 ff.), are frequently used as filling material, especially in dentistry. Partners employed for curing (cement formation) are usually the polyalkenoic acids mentioned. Advantages of these materials are: little or no shrinkage through to an expansion caused by the ionomer reaction as a result of water uptake, presence of fluorides and phosphates desired, good bond with the tooth tissue due to the acid groups in the matrix. However, use in dentistry would also require excellent mechanical properties, a favorable abrasion performance (e.g. during chewing) and good polishability of the fillings. These requirements are not, however, met by the cements mentioned owing to the size and shape of the ionomer particles. Thus, the sharp edges, the size and asymmetry of the particles result in those in the positions near the surface being torn from the cement composite during chewing or polishing, which increases abrasion and makes it virtually impossible to achieve a smooth surface. Additional disadvantages are the lack of ability to be adapted to special problems such as X-ray opacity or specific requirements in respect of transparency, e.g. index of refraction or the like.

It is therefore an object of the present invention to provide ionomer particles of the type mentioned at the outset which do not have the abovementioned disadvantages and in combination with any, preferably acid-modified matrix systems lead to cements which are mechanically more stable than the known particles.

This object is achieved by the provision of ionomer particles which have a spherical or approximately spherical shape.

The ionomer particles are either purely inorganic particles, or they can be organically modified.

The novel ionomer particles preferably have a diameter smaller than that which is presently customary. The particle size can be set, for example, in the range from 5 nm to 50 $\mu$m. This can be achieved using various, simple methods, which is explained in more detail further below.

The spherical ionomer particles of the present invention have an inner region and also an outer region which comprises silicon ions and whose cations comprise (a) at least one element which in siliceous compounds can occupy lattice sites of silicon to produce a negative charge excess and (b) at least one element which can compensate the negative charge excess and is selected from among elements of main groups I and II and elements which can occur in divalent form. The cations of group (b) serve to effect the primary curing in the unstable phase, while those of the group (a) serve to effect secondary curing and the formation of the stable phase.

The expressions "silicon ions" and "cations" indicate that the elements concerned are present in bound form, but are not intended to rule out their incorporation in structures having some degree of covalent bonding.

The particles can further comprise appropriate additives, for example phosphate (e.g. as aluminum or calcium phosphate) or fluoride (e.g. as NaF, $CaF_2$ or $AlF_3$).

The spherical ionomer particles preferably contain cluster-like, silicate-containing regions. In a further preferred embodiment of the invention, the ionomer particles are entirely homogeneous. In a third preferred embodiment, they consist of an inner region or core which can have a composition different from that of the outer region (the "shell"), in which case the shell can consist of one or more layers. However, it is in each case essential for the outer region, i.e. at least the outermost layer, to have the abovementioned composition. If the structure with an inner region different from the outer region is chosen, this can, if desired, be inert toward leaching and serve as carrier for further properties.

In addition, the surface of the particles can be silanized, which makes incorporation into some matrices easier. Silanization can be carried out by known methods, either in-situ or subsequently depending on the method employed.

The particles can be completely solid (dense) or may have a porous structure.

The particle size can vary as a function of production conditions; it can, if desired, be set within a narrow range. Preference is given to providing relatively small particles, since these have more surface area. As a result, the reactivity is increased and thus the curing of the cement is accelerated or improved. A further advantage of smaller particles is improved translucence of the cement formed. Examples of particle sizes are, for example, from 20 nm to 20 $\mu$m or from 0.5 $\mu$m to 50 $\mu$m; the particle size chosen in each case can then be achieved in a very narrow distribution range which can be significantly less than one power of ten. Smaller particles, e.g. in the range from 50 nm to 1 or 2 $\mu$m, are particularly suitable for dental fillings. Apart from the above-described advantages, small particles also allow a particularly high proportion of ionomer to be incorporated. In order to be able to obtain a very particularly high proportion of ionomer in the cement, a specific embodiment of the invention provides a mixture of two or three lots of ionomer particles which each have a defined narrow size distribution whose size ratio to the other lots is such that the smaller particles fit into the gaps of a conceptual close packing of spheres of the larger particles and, if present, the still very much smaller particles fit into gaps in the resulting packed arrangement. This embodiment, too, is particularly suitable for dental fillings because a high ionomer content in the cement can be achieved. However, the invention provides not only relatively small particles but also relatively large particles, whether as largest fraction of a size mixture as described above or for use of the cements in other medical or non-medical fields (e.g. as bone replacement or as adhesive).

The spherical ionomer particles can be produced by various methods. Here, a dispersion comprising organic components is formed, and a controlled hydrolysis and condensation proceeds in this dispersion. The expression "dispersion" is used here although it is also possible for genuine solutions, suspensions or emulsions to be obtained or to be formed in particular stages of the hydrolytic condensation. Sol and gel formation processes are also encompassed by the expression (e.g. the disperse phase of a dispersion or emulsion can gel). It is therefore to be understood in appropriately broad terms. The dispersion can be converted into spherical particles in various ways, e.g. by the Stober process or spray drying. As organic component, use is made of at least one compound which is selected from among organosilicon compounds and organic compounds of the cations of the elements specified under (a) and (b). The expression "organic compound" is intended to refer to any "organometallic" compound which has at least one organic constituent bound or complexed to the metal via oxygen or an organic constituent bound to the metal in such a way that at least partial hydrolysis of this compound can occur in the presence of water, aqueous or other solvents or dispersion media (e.g. alcohols), which hydrolysis may possibly only start in the presence of acid or base, after which the compound undergoes a controlled condensation so that chain or network condensates are formed in the "solvent" but no uncontrolled precipitation reactions occur (the expression "solvent" is naturally to be interpreted in such a way that the medium generally does not form a genuine solution of the organic compound(s) but usually forms a suspension, a dispersion, an emulsion, a sol or a gel) . Examples of organic compounds are oxo complexes such as alkoxides or carboxylates, but also other suitable metal complexes or organometallic compounds. Depending on requirements, a plurality, or all, of the cations of the subsequent spherical particles can be used in the form of the abovementioned organic compounds.

Elements which can be used under (a) are preferably those of main group III, i.e. boron, aluminum, gallium, indium and thallium. Further suitable elements are scandium, yttrium and rare earths such as lanthanum, cerium, gadolinium, ytterbium. Owing to the favorable structures of aluminosilicates, aluminum is preferred. The selection of specific elements, e.g. very heavy elements, enables particular properties such as X-ray opacity to be produced.

If the element or one (or all) of the elements specified under (a) is to be used as organic component, preference is given to using oxo complexes for this purpose. Suitable oxo complexes are, for example, alkoxides, diketonates and carboxylates. Examples of alkoxides are ethoxide, secondary and tertiary butoxide, e.g. of aluminum. Examples of carboxylates are those of oxalic acid and methacrylic acid. Acetates or acetylacetonates and also further complexes with chelating agents are also possible. If instead or additionally one or the (or all) element(s) specified under (a) is/are not to be used as organic component, use in the form of possibly extremely fine powders of the corresponding inorganic compounds which may be soluble or insoluble in the solvent selected, e.g. oxides, halides (chlorides, fluorides), phosphates or other salts (e.g. $AlCl_3$), is possible.

The metals among which the cations of the group specified under (b) can be selected encompass, for example, lithium, sodium, potassium, rubidium, cesium, beryllium, magnesium, calcium, strontium and barium, tin or zinc (the latter in its divalent form). The selection of suitable cations enables specific properties to be generated in a targeted way, for example X-ray opacity, reactivity, optical properties or the like.

When the element or one (or all) of the elements specified in group (b) is to be used as organic component, possible compounds are, not only but in particular, the carboxylates and alkoxides. Particular preference is given to magnesium acetate, calcium acetate and strontium acetate and the alkoxides, e.g. isopropoxides, of these elements. If instead or additionally one or the (or all) element(s) specified under (b) is/are not to be used as organic component, use in the form of possibly extremely fine powders of the corresponding inorganic compounds which may be soluble or insoluble in the solvent chosen, e.g. oxides, halides (chlorides, fluorides), phosphates or other salts (e.g. $MgCl_2$, $SnCl_2$), is possible.

The silicon ions required for the outer region can be incorporated into the ionomer particles in various ways.

Thus, for example, hydrolyzable silanes or siloxanes, for example alkylsilanes and/or alkoxysilanes, can be added to the dispersion. In this case, particles having a homogeneous silicate-containing matrix in the outer region are obtained. Alternatively, a dispersion comprising compounds of the complexed elements specified in group (a) and/or in group (b) can, for example be admixed with a second dispersion of silicon dioxide particles having a very small diameter. In this case, the silicon dioxide forms cluster-like structures within the outer region of the resulting particles which, owing to their small diameter, are very well crosslinked with the oxides of the other elements.

Depending on the field of application, various further substances can be mixed into the abovementioned dispersion. An example is the incorporation of tin dioxide particles into- a sol comprising the abovementioned constituents. In this way, it is possible to obtain spherical particles which have an inner region of tin dioxide and, for example, achieve good X-ray absorption. The core of the ionomer particles can instead comprise silicon dioxide; for this purpose, silicon dioxide particles of the appropriate size (e.g. having a diameter of 30–100 nm (e.g. for dental purposes) or from 1 to 2 $\mu$m) are brought into contact with the dispersion, so that the latter can deposit in the outer region around the silicon dioxide core. The abovementioned ionomer-reactive modifications are mentioned only by way of example; all possible variants can be employed as long as the ionomer particles have the abovementioned ionomer-reactive constituents in their outer region.

The abovementioned organically modified constituents for producing the dispersion can, for example, be introduced into water and, if desired, admixed with acetic acid or glacial acetic acid (or be introduced into the previously acidified solvent). Basic solvents are also possible. As an alternative, the organically modified components, for example in a nonaqueous dispersion medium, e.g. an alcohol, can be admixed in an appropriate way with an amount of water sufficient for the required hydrolysis processes and, if desired, with base or acid as catalyst. Beforehand or afterwards, any inorganic-substances to be processed together with the ionomer can be incorporated; these inorganic substances may, if desired, previously have been dissolved or dispersed. In this environment, hydrolytic condensation of the organically modified constituents commences, but the reaction conditions have to be regulated so that hydroxides or oxides do not precipitate in an uncontrolled manner. Rather, the constituents are converted into chains and/or a network in which the hydrogen bonds present are sufficient to obtain a stable framework throughout the space from which the particles develop (i.e. a dispersion or suspension) or throughout the entire liquid (with formation of a sol or gel).

The above-described constituents form a dispersion which, according to the invention, is converted into spherical or approximately spherical particles, or are separated off from such particles. This can be done in various ways.

The prior art discloses a series of processes which can, for example, be utilized for producing the ionomer particles of the invention.

Stöber and Fink (Journal of Colloid and Interface Science 26, 62–69 (1968)) describe the production of agglomerate-free, monodisperse silica particles starting from tetraalkoxysilanes and water in alcohol in the presence of ammonia as catalyst (generally known as the Stober process). The particle size can be adjusted within the range from 50 to 2000 nm via various parameters such as water concentration, ammonia concentration, choice of alkoxysilane and temperature.

EP 216 278 describes a process based on the Stober process for producing monodisperse, nonporous silica particles which have a size of from 50 to 10,000 nm and whose monodispersity has been optimized to less than 5%.

On the basis of the Stober process, DE-C 3247800 describes the production of spherical, amorphous mixed particles based on silica and from 0.01 to 20 mol % of an oxide of a metal of groups I-IV of the Periodic Table.

DE 38 34 774 gives a review of the state of the art of the emulsion process for water-in-oil emulsions (W/O). Minehan and Messing (Colloids and Surfaces 63, 181 to 187 (1992)) describe the production of silica particles via oil-in-water emulsions (O/W). Microemulsion methods are known for producing nanosize particles (<100 nm), for example the production of $SiO_2$ particles in nonionic multicomponent systems, as described by K. Osseo-Asare, F. J. Arrigada, Colloids and Surfaces 50, 321–339 (1990). Particles having a size range of 50–70 nm with standard deviations of less than 8.5% are obtained.

Various solution aerosol thermolysis (SAT) processes, e.g. spray drying, are known for producing powders (G. V. Jayanthi, S. C. Zhang, G. L. Messing, Aerosol Science and Technology, 19, 478–490 (1993)). SAT represents a class of production processes in which a precursor liquid is sprayed by means of nozzles into a preheated oven. Alternatively, it is also possible to use a chopper (R. N. Berglund et al., Environ. Sci. Technol. 1973, 7 (2), 147–153). The resulting droplets are, depending on the diameter of the nozzle or the chopper frequency, in the range from less than 1 $\mu$m to more than 50 $\mu$m. The solvent vaporizes at the high temperatures in the oven, so that dry powders are formed.

The abovementioned processes can be utilized in principle for producing the spherical or approximately spherical ionomer particles of the invention. In place of the hydrolyzable compounds employed in the above processes, it is necessary for the organic and any other compounds which are essential in the present invention to be introduced into the liquid.

According to the invention, it is possible, for example by means of a method based on the Stöber process, to apply a shell containing silicon ions and additional elements of groups a) and b) to various inert particle cores (e.g. $SiO_2$, $SnO_2$ cores). As cores, it is possible to use monodisperse, spherical nuclei produced in any way. Examples of suitable cores are commercially available, agglomerate-free, monodisperse, spherical $SiO_2$ (e.g. Ludox, DuPont) or $SnO_2$ particles. Using a method based on the abovementioned Stöber process, it is also possible to produce monodisperse spherical $Sio_2$ cores in a size range from 50 to 2000 nm which are then provided with a "shell".

To apply the shell, organosilicon compounds such as, for example, alkoxysilanes in combination with compounds of groups a) and b) (the two latter in organic or inorganic form) can be used as starting compounds. The organic compounds or a low molecular weight condensation product thereof are added in an amount of, for example, 1–40% by weight to a solvent, preferably an alcohol. This solution is titrated into a mother dispersion of the cores so that a supersaturation concentration which would lead to formation of new particles is not reached during the course of the growth process of the particles. Since the organic compounds are to be hydrolyzed in this process, water is added in a concentration matched to the concentration of the starting materials. Since the hydrolysis/condensation reactions proceed very slowly under neutral conditions, an acidic or alkaline medium is preferred. For the purposes of the present invention, it has been found that a pH of 8–9 is advantageous for uniform growth of the particles and that ideally spherical, monodisperse ionomer particles result. These have a surprisingly rapid ionomer reaction.

In-situ surface modification can be achieved, for example, by addition of a silane, e.g. aminopropyltriethoxysilane or methacryloxypropyltrimethylsilane, in the form of a 1–100% strength by weight solution to the dispersion. As solvent, preference is given to using the same solvent as that of the mother dispersion, for example ethanol. It is likewise possible to surfacemodify the dried particles afterwards. For this purpose, the particle powder is suspended in an amount of about 10% by weight in an organic solvent, e.g. toluene, the amount of silane necessary to form a monomolecular layer is added, a catalyst is introduced if desired and, if desired, the mixture is refluxed.

The Stöber process can, of course, also be used for producing homogeneous or other particles without a core. The conditions then have to be chosen so that particle formation is induced.

Furthermore, it has been found that emulsion processes are also very well suited to producing the above-described ionomer particles. It is possible to use both the O/W method and the W/O method. Preference is given to using the W/O method (see, for example, EP 0363927). The proportion of aqueous phase is preferably from about 15 to 45% by volume, while that of the emulsifier is preferably from about 1 to 20% by weight. During the emulsion process, precipitation or gel formation, preferably induced by a basic pH shift, takes place in the aqueous droplets. Suitable starting compounds are salts and organic complexes of the above-described elements, preferably nitrates, alkoxides and acetates, and also any dispersions produced therefrom. The ionomer particles obtained surprisingly have a narrow size distribution which can be significantly less than one power of ten.

The above-described liquid can instead be subjected to an aerosol treatment, in particular spray drying. For example, very finely divided $SiO_2$ particles or silicon alkoxides can be mixed with alkoxides or carboxylates of the cations of groups a) and b) in an aqueous solution having a pH of <7. Spherical-shaped droplets are sprayed by means of suitable nozzles. These droplets can, if desired, be dried, for example at about 250° C., until the volatile organic constituents have been removed.

In all the processes, the particles obtained can, after removal of the solvent or after separation from the solvent, can, if desired, be subjected to a pyrolysis if organic constituents are still present (for example at from 400° to 600° C.). This produces organic-free siliceous ionomer particles.

Depending on the starting compounds used, ionomer particles of differing structure are formed in the abovementioned process. The particles can have a fully homogeneous structure or else have silicate-containing regions together with calcium aluminosilicates, strontium aluminosilicates or the like or regions comprising exclusively silicon as cations together with regions comprising calcium and/or strontium, aluminum and silicon or the like. The ionomer particles can consist exclusively of these structures or else can have a discreet inner region which has a different composition, for example silicon dioxide, tin dioxide, a mixture of the two, aluminum silicate or the like. In a specific embodiment, the spherical ionomer particles consist of an inner region and a plurality of outer, preferably shell-like, regions. These can be produced, for example, by enveloping silicon dioxide particles of suitable size with a first gel or sol, drying and, if appropriate, pyrolyzing them, and then enveloping the resulting particles with a second gel or sol having a different composition, drying and, if appropriate, pyrolyzing again. At least the second gel or sol has to have a composition as described above. The spherical ionomer particles of the invention can also be silanized or otherwise surface-modified in a customary manner, although this will generally not be necessary.

Incorporation of the ionomers of the invention into matrix systems, preferably into acid-containing matrix systems, results after the above-described two-staged curing in new types of materials, e.g. composites, cements, compomers. Their properties can, as described above, be set in a targeted way by use of appropriate starting materials, e.g. by addition of X-ray-opaque constituents or by means of reaction conditions (e.g. concentrati on, temperature, pH) which allo w the diameter of the particles to be varied. These materials are particularly usef ul in dentistry (e. g. as filling material) and in the medical sector (e.g. as bone cement). Furthermore, materials having a different transparency, color and a different index of refraction can be used.

It has surprisingly been found that the spherical shape and size of the ionomer particles of the invention lead to significantly imp roved abrasion re sistance and mechanical properties of dental fillings when the particles are processed together with alkenoic acids to produce a cement. Furthermore, it was surprisingly found that the rate of the ionomer reaction and of cement formation is greatly increased and the degree of reaction has increased. This can be confirmed by means of IR spectroscopy.

Suitable matrix systems with which the ionomer particles of the invention can be processed to give cements are the abovementioned alkenoic acids, e.g. polyalkenoic acids (monocarboxylic, dicarboxylic or tricarboxylic acids) such as polyacrylic acid, polyitaconic acid, polymaleic acid or copolymers of these acids, to which, if desired, hydroxycarboxylic acids such as citric acid or tartaric acid can be added. These can be employed in an aqueous phase or freeze-dried; in the latter state, water naturally has to be added when making up the mixture with the ionomers. However, other, preferably acidic matrix systems are also possible, e.g. polyphosphonic acids such as poly (vinylphosphonic acid), systems which further comprise light-curable constituents or matrices which can form the above-described compomers with ionomer particles.

EXAMPLE 1 ($SiO_2$/CaO/$Al_2O_3$ Particles, Molar Ratio:Si/Ca/Al=1:1:1)

Figure 1:
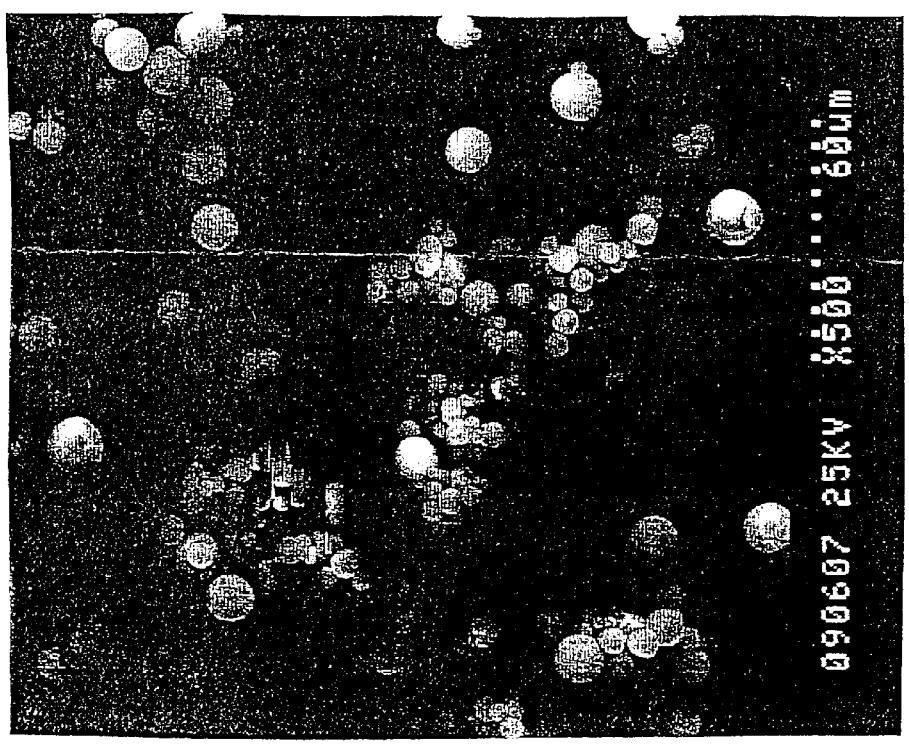

7.6 g of aluminum sec-butoxide were admixed at RT with 40 ml of water and glacial acetic acid while stirring. A solution of 4.7 g of calcium acetate in 20 ml of water and 1 ml of concentrated acetic acid was added thereto while stirring. A dispersion obtained by dilution of 5 g of commercially available $SiO_2$ particles (Ludox AS 40) with 45 g of water and dropwise addition of 1 ml of concentrated acetic acid was added dropwise to the resulting mixture. Spray drying at about 250° C. gave a white powder which, according to SEM, consists of spherical particles. XRF analyses confirm an Si/Al/Ca ratio equal to that of the starting materials. A temperature treatment at 500° C. for 3 hours followed. FIG. 1 shows a scanning electron micrograph of the particles formed.

To confirm cement formation and thus the practical usefulness of the particles synthesized, the particles were incorporated into a resin comprising carboxylic acid and subjected to storage under water. Curing of the mixture in the manner of an ionomer reaction occurred, and was confirmed by FTIR spectroscopy of the COO—Al and COO—Ca bonds formed indicated by vibrations at about 1560 or 1450 to 1410 $cm^{-1}$.

EXAMPLE 2 (SiO$_2$/SnO$_2$/SrO/Al$_2$O$_3$ Particles; Molar Ratio:Si/Sn/Sr/Al=1:1:1:2)

14.2 g of aluminum sec-butoxide were admixed at RT with 80 ml of water and glacial acetic acid while stirring. A solution of 5.93 g of strontium acetate in 50 ml of water and 1 ml of concentrated acetic acid was added thereto while stirring. A mixture of 4.33 g of a commercially available 40% strength by weight aqueous SiO$_2$ dispersion, 28.9 g of a commercially available 15% strength by weight aqueous SnO$_2$ dispersion, 150 ml of water and 1 ml of concentrated acetic acid was slowly added dropwise to this mixture. Spray drying at about 250° C. gave a white powder. XRF analyses confirm an Si/Sn/Sr/Al ratio equal to that of the starting materials. A temperature treatment at 500° C. for 3 hours followed. FIG. 2 shows a scanning electron micrograph of the particles formed.

To confirm cement formation and thus the practical usefulness of the particles synthesized, the particles were incorporated into a resin comprising carboxylic acid and subjected to storage under water. Curing of the mixture in the manner of an ionomer reaction occurred, and was confirmed by FTIR spectroscopy of the COO—Al and COO—Sr bonds formed indicated by vibrations at about 1555 or 1455 to 1400 cm$^{-1}$.

EXAMPLE 3 (SiO$_2$ Nuclei and Coating with Si/Ca/Al-containing precursors)

3.1. Preparation of Monodisperse SiO$_2$ Nuclei 45 ml of 25% strength ammonia are added to 900 ml of ethanol in a 11 conical flask and stirred. To this solution at 25° C., 45 g (0.2 mol) of tetraethoxysilane at the same temperature are added. This gives a dispersion containing particles having a mean size of 60 nm with a standard deviation of <10% (dynamic light scattering, transmission electron microscopy).

3.2. Coating with Si/Ca/Al-containing precursors 1 g of the SiO$_2$ nuclei described under 3.1 are dispersed in 70 ml of anhydrous isopropanol. The pH is adjusted solution B is prepared by admixing 25 mg of Ca under an inert gas atmosphere with 130 ml of isopropanol, stirring for 1 hour at room temperature and subsequently heating to boiling. 140 mg of aluminum sec-butoxide and 1.0 g of tetraethoxysilane are added dropwise and the mixture is heated under reflux. After cooling to RT, solution B is added to the particle dispersion and the mixture is then stirred for another 10 hours. The subsequent washing procedure encompasses redispersion in isopropanol twice and isolation by means of centrifugation. XRF analyses confirm an Si/Ca/Al ratio equal to that of the starting materials. The mean size of the particles is 75 nm with a standard deviation of <10% (DLS).

To confirm cement formation and thus the practical usefulness of the particles synthesized, the particles are incorporated into a resin comprising carboxylic acid and subjected to storage under water. Curing of the mixture in the manner of an ionomer reaction occurs, and is confirmed by FTIR spectroscopy of the COO—Al and COO—Ca bonds formed indicated by vibrations at about 1560 or 1450 to 1410 cm$^{-1}$.

EIXAMPLE 4 (SiO$_2$ Nuclei and Coating with Si/Sr/Al-containing precursors)

4.1. Preparation of monodisperse nuclei 18 ml of 25% strength ammonia and 12 ml of distilled water are added to 360 ml of ethanol in a 500 ml conical flask and stirred. To this solution at 25° C., 18 g of tetraethoxysilane at the same temperature are added. This gives a dispersion containing particles having a mean size of 185 nm with a standard deviation of <10% (dynamic light scattering, transmission electron microscopy).

4.2. Coating with Si/Sr/Al-containing precursors 1 g of the SiO$_2$ nuclei described under 4.1 are dispersed in 70 ml of anhydrous isopropanol. The pH is adjusted to 9 using 0.1N HCl solution. In parallel thereto, a solution B is prepared by admixing 50 mg of Sr under an inert gas atmosphere with 130 ml of isopropanol, stirring for 1 hour at room temperature and subsequently heating to boiling. 140 mg of aluminum sec-butoxide and 1.0 g of tetraethoxysilane are added dropwise and the mixture is heated under reflux. After cooling to RT, solution B is added to the particle dispersion and the mixture is then stirred for another 10 hours. The subsequent washing procedure encompasses redispersion in isopropanol twice and isolation by means of centrifugation. XRF analyses confirm an Si/Sr/Al ratio equal to that of the starting materials. The mean size of the particles is 190 nm with a standard deviation of <10% (DLS).

To confirm cement formation and thus the practical usefulness of the particles synthesized, the particles are incorporated into a resin comprising carboxylic acid and subjected to storage under water. Curing of the mixture in the manner of an ionomer reaction occurs, and is confirmed by FTIR spectroscopy of the COO—Al and COO—Sr bonds formed indicated by vibrations at about 1555 or 1455 to 1400 cm$^{-1}$.

EXAMPLE 5 (SiO$_2$ Nuclei and Coating with Si/Sr/Al-containing precursors)

5.1. Preparation of monodisperse SiO$_2$ nuclei: see Example 3.1.

5.2. Coating with Si/Sr/Al-containing precursors 1 g of the SiO$_2$ nuclei described in Example 3.1. are dispersed in 70 ml of anhydrous isopropanol. The pH is adjusted to 9 using 0.1N HCl solution. In parallel thereto, a solution B is prepared by admixing 50 mg of Sr under an inert gas atmosphere with 130 ml of isopropanol, stirring for 1 hour at room temperature and subsequently heating to boiling. 140 mg of aluminum sec-butoxide and 1.0 g of tetraethoxysilane are added dropwise and the mixture is heated under reflux. After cooling to RT, solution B is added to the particle dispersion and the mixture is then stirred for another 10 hours. The subsequent washing procedure encompasses redispersion in isopropanol twice and isolation by means of centrifugation. XRF analyses confirm an Si/Sr/Al ratio equal to that of the starting materials. The mean size of the particles is 75 nm with a standard deviation of <10% (DLS).

To confirm cement formation and thus the practical usefulness of the particles synthesized, the particles are incorporated into a resin comprising carboxylic acid and subjected to storage under water. Curing of the mixture in the manner of an ionomer reaction occurs, and is confirmed by FTIR spectroscopy of the COO—Al and COO—Sr bonds formed indicated by vibrations at about 1555 or 1455 to 1400 cm$^{-1}$.

EXAMPLE 6 (Coating of SnO$_2$ Nuclei with Si/Sr/Al-containing precursors)

1 g of commercially available SnO$_2$ nuclei (Ø: 10 nm) are dispersed in 50 ml of water and diluted with 250 ml of isopropanol. The pH is adjusted to 9 using 0.1N HCl solution. In parallel thereto, a solution B is prepared by admixing 50 mg of Sr under an inert gas atmosphere with 130 ml of isopropanol, stirring for 1 hour at room temperature and subsequently heating to boiling. 140 mg of aluminum sec-butoxide and 1.0 g of tetraethoxysilane are added dropwise and the mixture is heated under reflux. After cooling to RT, solution B is added to the particle dispersion and the mixture is then stirred for another 10 hours. The subsequent washing procedure encompasses redispersion in isopropanol twice and isolation by means of centrifugation. XRF analyses confirm an Si/Sn/Sr/Al ratio equal to that of the starting materials. The mean size of the particles is 20 nm with a standard deviation of <10% (DLS).

To confirm cement formation and thus the practical usefulness of the particles synthesized, the particles are incorporated into a resin comprising carboxylic acid and subjected to storage under water. Curing of the mixture in the manner of an ionomer reaction occurs, and is confirmed by FTIR spectroscopy of the COO—Al and COO—Sr bonds formed indicated by vibrations at about 1555 or 1455 to 1400 $cm^{-1}$.

It has been found that the X-ray absorption of the ionomer particles increases in the order of the compositions from Example 3 to Example 6. This is in agreement with the incorporation of increasingly heavy elements in the order Ca (Ex. 3), Sr (Ex. 4 and 5) and finally Sn (Ex. 6).

EXAMPLE 7 (Surface Modification)

1 g of the ionomer particles obtained in Example 5 are dispersed in 100 g of toluene, 2 g of methacryloxypropyltriethoxysilane are added thereto and the mixture is heated to boiling for 5 hours. After cooling to RT, the particles are isolated by means of centrifugation and washed twice with toluene by means of redispersion/centrifugation cycles. Drying is carried out for 7 hours at 100° C. in an oil pump vacuum. The modification is confirmed by means of diffuse reflection infrared fourier transform spectroscopy (drifts) using vibrations at 1720 and 1636 $cm^{-1}$ specific to C=O and C=C double bonds.

What is claimed is:

1. Spherical or approximately spherical ionomer particles having an inner region and an outer region which comprises silicon ions and whose cations comprise (a) at least one element which in siliceous compounds can occupy lattice sites of silicon to produce a negative charge excess and (b) at least one element which is selected from among the elements of main groups I and II and elements which can occur in divalent form and can compensate the negative charge excess.

2. Spherical ionomer particles as claimed in claim 1, wherein the outer region is an oxidic region.

3. Spherical ionomer particles as claimed in claim 1, wherein the inner and outer regions are identical.

4. Spherical ionomer particles as claimed in claim 1, having a homogeneous distribution of the constituents.

5. Spherical ionomer particles as claimed in claim 1, having cluster-like regions of inert constituents.

6. Spherical ionomer particles as claimed in claim 1, wherein the inner region differs chemically from the outer region.

7. Spherical ionomer particles as claimed in claim 6, wherein the inner region comprises silicon dioxide and/or tin dioxide.

8. Spherical ionomer particles as claimed in claim 1, wherein the cations of group (a) are aluminum cations and the cations of group (b) are calcium ions and/or strontium ions.

9. Spherical ionomer particles as claimed in claim 1, wherein the outer region is surface-modified by silanization.

10. A process for producing spherical or approximately spherical ionomer particles as claimed in claim 1, comprising the following steps:

(i) forming a dispersion, a suspension, a solution, an emulsion, a gel or a sol using (1) at least one organosilicon compound or either silicon dioxide and/or at least one organic salt of silicon; and (2) at least one organic compound of at least one cation of the elements specified in claim 1(a) or either at least one oxide and/or inorganic salt of this element; and (3) at least one organic compound of at least one cation of the elements specified in claim 1(b) or either at least one oxide and/or inorganic salt of this element;

provided that at least one of components (1), (2) or (3) is selected from among the said organosilicon compounds and the organic compound of the cations of the elements specified in claim 1(a) and (b), in a suitable liquid medium (ii) effecting at least a partial hydrolysis and condensation of the component(s) specified under (1), (iii) producing spherical or approximately spherical particles in or from the liquid medium, and (iv) drying the spherical or approximately spherical particles.

11. The process as claimed in claim 10 further comprising the following step:

heating the dried particles to at least a temperature at which any organic constituents still present in the particles are removed.

12. The process as claimed in claim 10, wherein the particles are produced by an aerosol process, in particular by spray drying.

13. The process as claimed in claim 10, wherein the dispersion, suspension, gel or sol is formed with additional use of oxidic particles whose diameter is below that of the ionomer particles to be produced, preferably by 1–10%.

14. The process as claimed in claim 10 further comprising the steps:

(o) producing a particle dispersion by careful hydrolysis of a metal alkoxide in alcoholic solution, separating the particles obtained from the suspension, and using the particles for obtaining the dispersion, suspension, gel or sol as set forth under (i) in claim 10.

15. The process as claimed in claim 10, wherein the particles are formed by producing an emulsion, a dispersion or a suspension, whereupon they are separated from the surrounding solvent or the surrounding solvent is removed.

16. The process as claimed in claim 10, wherein the organic component(s) is/are selected from among alkoxysilanes, aluminum alkoxides and calcium acylates.

17. The process as claimed in claim 16, wherein the organic components are selected from among aluminum butoxide and calcium acetate and additional use is made of silicon dioxide.

18. The use of spherical or approximately spherical ionomer particles as claimed in claim 1, in dental cements, bone cements or adhesives.

19. The use of spherical or approximately spherical ionomer particles as claimed in claim 1, to together with polyacids, in particular polyalkenoic acids, as cement.

20. The process according to claim 10 wherein in step (iii), the spherical or approximately spherical particles are separated off from the liquid medium.

21. The process according to claim 14, wherein in step (o), the hydrolysis of a metal alkoxide in alcoholic solution is an acid- or base-catalyzed hydrolysis.

22. The process according to claim 14, wherein, after separation of the particles obtained from the suspension, the particles are dried and/or heated to drive off organic material still present.

* * * * *

UNITED STATES PATENT AND TRADEMARK OFFICE
CERTIFICATE OF CORRECTION

PATENT NO. : 6,447,907 B1 Page 1 of 1
DATED : September 10, 2002
INVENTOR(S) : Herbert Wolter and Carsten Gellermann It is certified that error appears in the above-identified patent and that said Letters Patent is hereby corrected as shown below:

<u>Column 6,</u>
Line 49, the formula "Sio$_2$" should read -- SiO$_2$ --.

<u>Column 7,</u>
Line 6, "methacryloxypropyltrimethylsilane" should read
-- methacryloxypropyltrimethoxysilane --.

<u>Column 8,</u>
Line 13, the word "concentrati on" should read -- concentration --.
Line 14, the word "allo w" should read -- allow --.
Line 15, the word "usef ul" should read -- useful --.
Line 21, the word "imp roved" should read -- improved --.

<u>Column 9,</u>
Line 37, please add after the word "adjusted", -- to Ph 9 using 0.1 HCl solution.
In parallel thereto, a --.
Line 60, the word "EIXAMPLE" should read -- EXAMPLE --.

<u>Column 11,</u>
Lines 25 and 26, "methacryloxypropyltriethoxysilane" should read
-- methacryloxypropyltrimethoxysilane --.

Signed and Sealed this

Twenty-second Day of July, 2003

JAMES E. ROGAN
*Director of the United States Patent and Trademark Office*